United States Patent [19]

McDavid, III

[11] Patent Number: 4,805,606
[45] Date of Patent: Feb. 21, 1989

[54] KNEE BRACE

[75] Inventor: Robert F. McDavid, III, Downers Grove, Ill.

[73] Assignee: Terrence M. Fee, Clarendon Hills, Ill.

[21] Appl. No.: 910,632

[22] Filed: Sep. 23, 1986

[51] Int. Cl.⁴ .............................................. A61F 5/00
[52] U.S. Cl. ...................................... 128/80 C; 2/22; 128/88
[58] Field of Search ................. 128/80 F, 80 C, 80 R, 128/88; 12/16, 22, 24

[56] References Cited

U.S. PATENT DOCUMENTS

| 2,467,907 | 4/1949 | Peckham | 138/88 |
| 3,528,412 | 9/1970 | McDavid | 128/80 C |
| 3,581,741 | 6/1971 | Rosman et al. | 128/80 C |
| 3,945,046 | 3/1976 | Stromgren | 128/80 C X |
| 4,381,768 | 5/1983 | Erichsen et al. | 128/80 C |
| 4,554,913 | 11/1985 | Womack et al. | 128/80 C |
| 4,572,170 | 2/1986 | Cronk et al. | 128/80 C |

FOREIGN PATENT DOCUMENTS 846895 8/1952 Fed. Rep. of Germany .

OTHER PUBLICATIONS

Advertising brochure: "OTI Brace", 4 pgs., by Orthopedic Technology, Inc. of San Leandro, Calif.
Advertising brochure: "Anderson Knee Stabler", 4 pgs., by Omni Scientific Inc. of Lafayette, Calif.
Advertising brochure: "Lerman Multi-Ligamentus Knee Control Orthosis", 2 pgs., by Zinco Industries, Inc. of Montrose, Calif., Copyright notice dated 1985.
Advertising brochure: "NuKO Camp", 6 pgs., by Camp International, Inc. of Jackson, Mich., Copyright notice dated 1984.
Advertising brochure: "The Lenox Hill Lightweight", 1 pg., by Lenox Hill Brace, Inc. of New York, N.Y.
Advertising brochure: "Lorus Knee Orthosis", 4 pgs., by Medical Designs, Inc. of Azle, Tex.
Advertising brochure: "The Leader in Knee Motion Management", 8 pgs., by DonJoy of Carlsbad, Calif.
Article: "An Orthosis for Medial or Lateral Stabilization of Arthritic Knees", by F. Cousins and James Foort, *Orthotics and Prosthetics*, vol. 29, No. 4, pp. 21–26, Dec. 1975.
Article: "Fabrication and Fitting of the CARS–UBC Knee Orthosis", by R. Wassen et al., *Orthotics and Prosthetics*, vol. 30, No. 2, pp. 3–11, Jun. 1976.
Advertising brochure: "C.T.I. Brace", by Innovation Sports of Irvine, Calif., 16 pgs., assembled in a folder, with the front page entitled Innovation Sports Update, dated Spring 1985.

*Primary Examiner*—David A. Wiecking
*Assistant Examiner*—Moshe I. Cohen
*Attorney, Agent, or Firm*—Fitch, Even, Tabin & Flannery

[57] ABSTRACT

A unilateral knee brace is provided with pliable, non-extensible tension members which are connected to the brace and are placed in tension and resist opening of the knee at the medial side of the knee. The preferred tension members are X-shaped straps which are crossed at the knee joint. More specifically, the knee brace has a hinged support including pivotally-connected upper and lower plate members extending above and below a wearer's knee. The hinged support is secured to the wearer's leg by upper and lower cuffs which encircle lateral or outside portions of the wearer's leg above and below the knee. The hinged support is positioned on a lateral or outside portion of the wearer's leg. The brace further includes a pliable support of non-elastic, stretch-resistant straps extending between the cuffs, and positioned opposite the hinged support on a medial or inner portion of a wearer's leg. Upper and lower free ends of the pliable support straps are connected to the hinged support plates. The non-elastic pliable straps maintain knee stiffness against medially-directed forces.

12 Claims, 3 Drawing Sheets

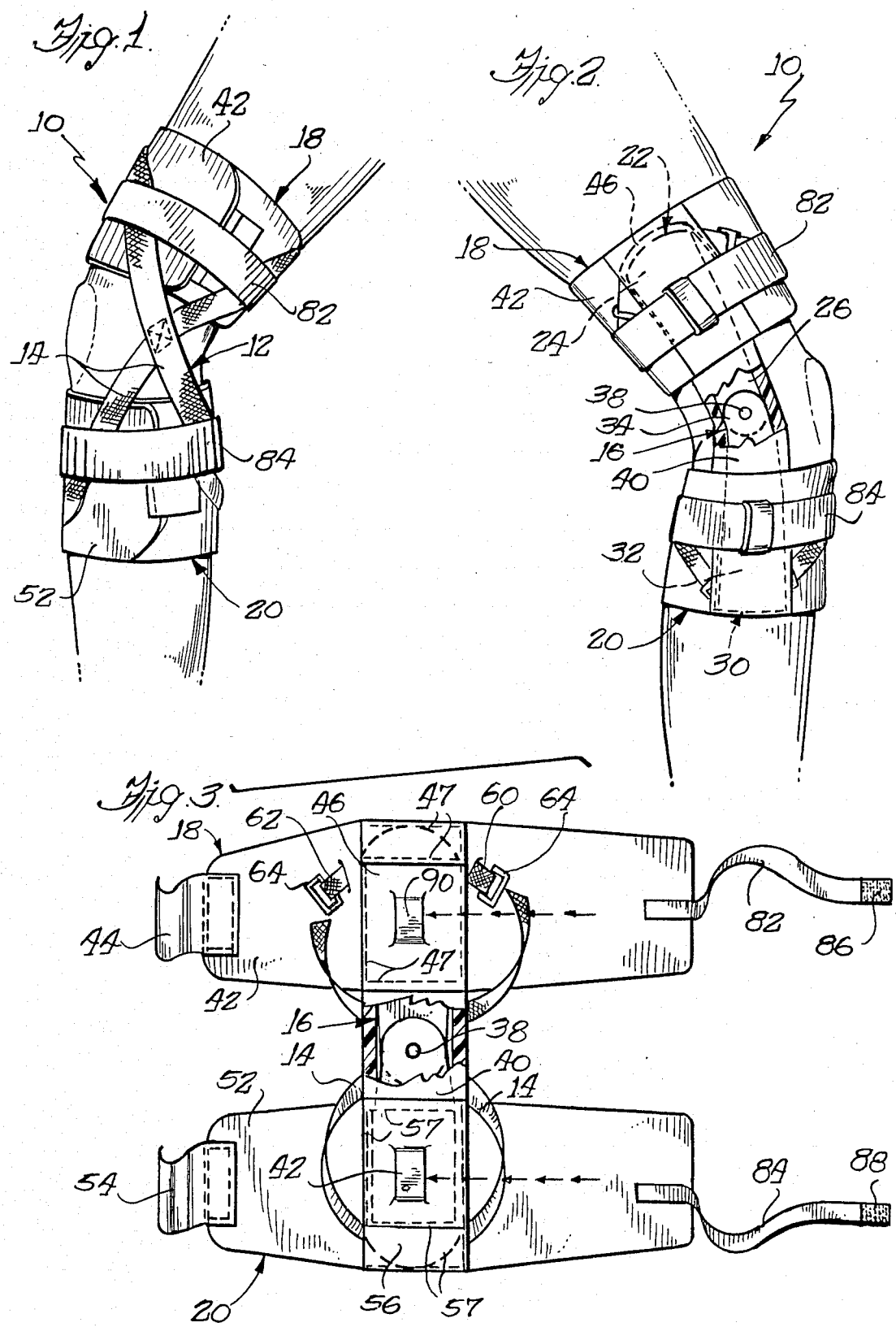

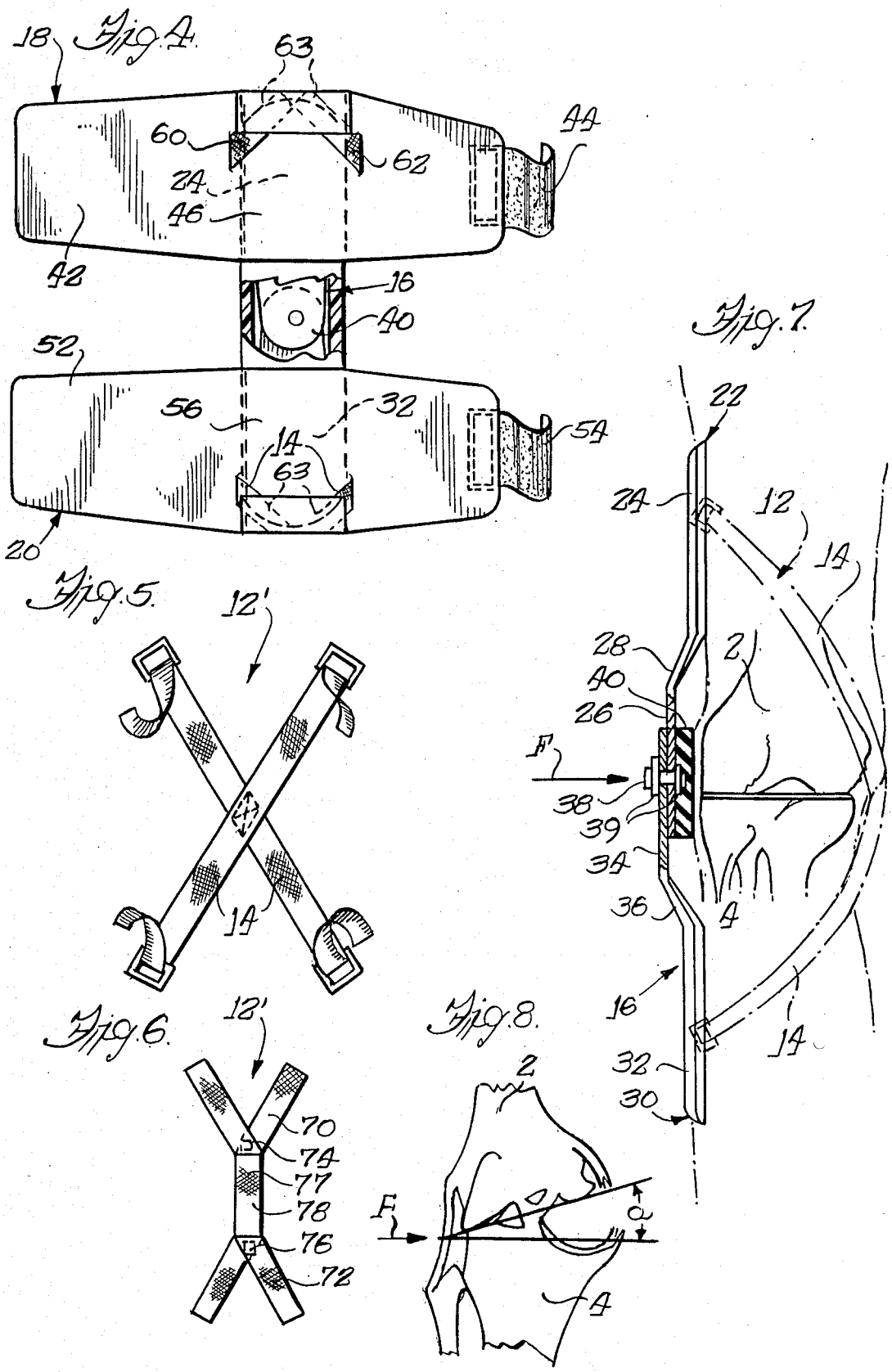

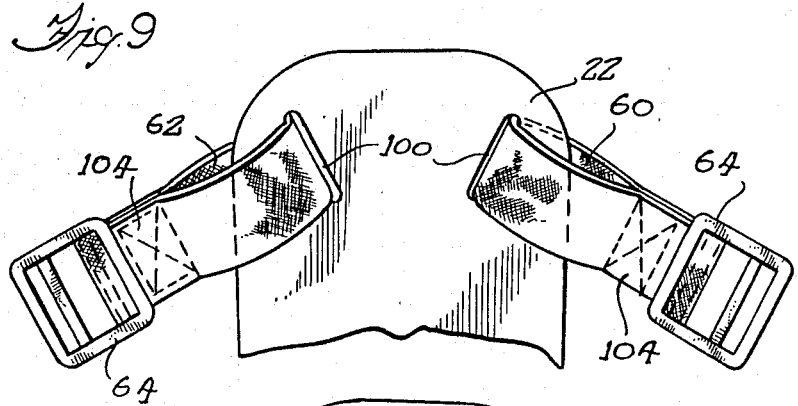
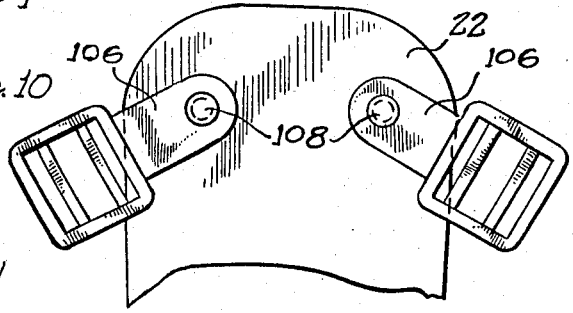
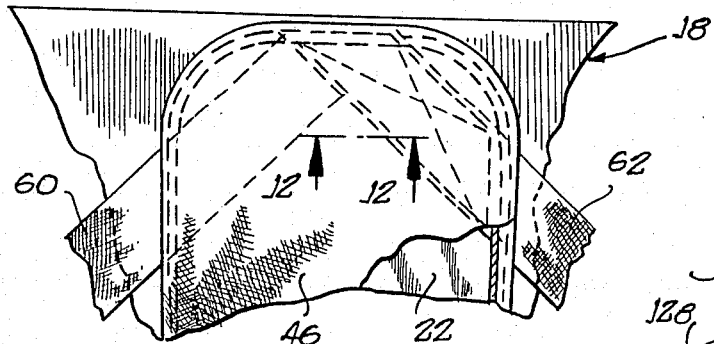
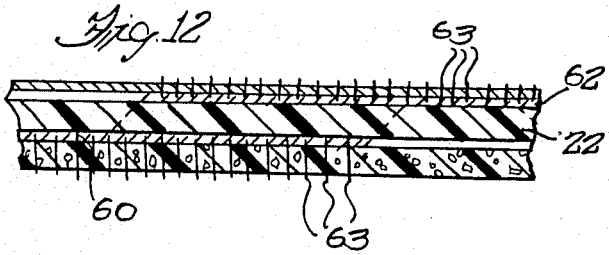
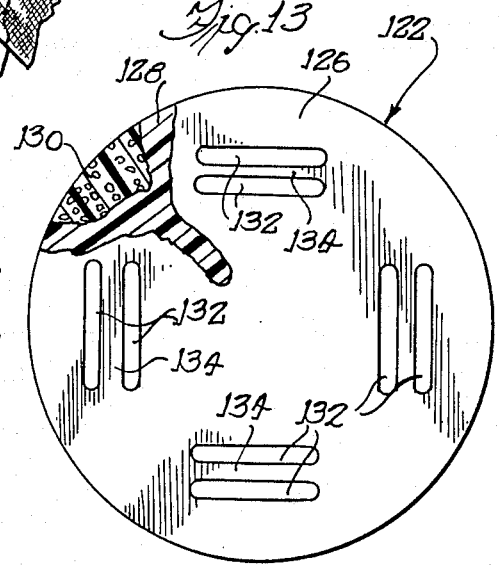

KNEE BRACE

BACKGROUND OF THE INVENTION

This invention generally relates to knee braces of the type having hinged support members and more particularly, the present invention pertains to unilateral knee braces.

The present invention is directed to braces which protect the wearer from tearing or other stressing of ligaments or cartilage on the medial or inside portion of the knee joint, as a result of a blow from the lateral side of the knee. Generally, forces applied to the outside of the knee joint tend to cause the knee joint to bend about the lateral portion, so as to open or separate the medial portion of the knee. This tensions a system of ligaments and cartilage spanning medial portions of the knee joint, which attempts to hold that region of the knee joint in a closed condition.

Generally, athletes involved in contact sports are exposed to greater potentially damaging forces than other individuals, and therefore require greater support if their knee joint is to be protected against medial separation. However, these individuals also need a brace that is lightweight and provides a full range of motion.

One example of a unilateral lightweight knee brace is given in U.S. Pat. No. 3,528,412, issued Sep. 15, 1970 to Robert F. McDavid. The term "unilateral" is used herein to refer to a brace having a hinged support on only one side of a wearer's knee. In that patent, a knee brace is described having pivotally connected upper and lower portions adapted for securement to the upper and lower leg portions of a user. Stop means limit pivotal movement between the upper and lower portions. The arrangement uses straps for securing the brace to the leg and a resilient covering for the brace to prevent medial and lateral separation or other displacement of the knee joint. Despite the generally fine performance of this brace, athletes and others who are subjected to greater contact forces are constantly searching for braces which offer increased support of the knee joint.

Another example of a unilateral lightweight brace is that manufactured by Scott Grey of Colorado which has upper and lower leg-wrapping cuffs located above and below the knee joint. A rigid two-piece hinged support extends between the cuffs on the outside or lateral portion of a wearer's leg. An X-shaped elastic strap assembly, located on the opposing inside or medial portion of the wearer's leg also extends between the cuffs, and is directly attached at either end of the hinged support to assist in holding the brace on the wearer's leg and at the knee joint as the leg is flexed and bent at the knee.

Some contact sports require improved support, without an increase in weight or bulk of the brace construction. Heavier and more bulky conventional alternatives to the above braces usually include two sets of hinged supports, one on each side of the knee. These bilateral braces can offer some improved resistance to distortion of the knee in lateral directions. However, such performance is achieved at the expense of additional bulk and weight, and a more complex assembly, which may impede athletic activity.

The present invention is also directed to lightweight knee braces of the type wherein a single hinge support contacts only the lateral or outside portion of a wearer's leg, as opposed to arrangements, such as that of U.S. Pat. No. 3,581,741 issued June 1, 1971 to Rosman, wherein U-shaped rigid cups engage three sides (posterior or anterior, as well as the lateral and medial sides) of a wearer's leg. Alternatively, the present invention utilizes leg-wrapping cuffs to secure the hinged support about a wearer's leg.

SUMMARY OF THE INVENTION

Accordingly, it is the primary object of the present invention to provide a lightweight knee brace of the unilateral type which provides improved support against medial separation of a wearer's knee.

These objects, as well as others that will become apparent upon reference to the following detailed description and accompanying drawings, are provided by a knee brace having a unilateral support which includes lower and upper plates positioned adjacent the lateral or outside portions of the wearer's leg. The lower and upper plate members extend below and above the wearer's knee, respectively, and the two plates are pivotally attached together adjacent the wearer's knee joint. A pliable support of stretch-resistant material extends between the two cuff members, and is positioned adjacent the medial or inside portion of the wearer's leg.

The pliable support may have a generally X-shaped cross section, with the center of the "X" overlying the knee, so as to oppose the pivotal connection of the hinged support. The pliable support may also take the form of two opposed V-shaped portions having generally opposed spaced-apart apices joined by a connector strap.

The free ends of the "X" or the free ends of each V-shaped portion are secured to a respective plate member, either directly, or through a rigid non-stretch attachment positioned immediately adjacent the plate member.

BRIEF DESCRIPTION OF THE DRAWINGS

FIG. 1 is a perspective view of a knee brace embodying the present invention illustrating the medial or inside portion of the wearer's leg;

FIG. 2 is a perspective view of a knee brace of FIG. 1 illustrating the lateral or outside portion of the wearer's leg;

FIG. 3 shows the outside of the knee brace of FIGS. 1 and 2, prior to assembly;

FIG. 4 shows the inside of the brace of FIGS. 1-3, prior to assembly;

FIG. 5 shows the medial strap arrangement of FIGS. 1-4 in greater detail;

FIG. 6 shows an alternate medial strap arrangement;

FIG. 7 shows a partial front view of the brace of FIGS. 1-5, showing the hinged and flexible support assemblies thereof.

FIG. 8 shows an anterior view of a knee joint, illustrating medial separation, protection against which is offered by the present invention;

FIGS. 9 and 10 show alternative embodiments for joining medial support straps to an upper hinge plate;

FIG. 11 is an enlarged portion of FIG. 4, showing an alternative method of joining a medial support strap to a cuff member;

FIG. 12 is a partial cross-sectional view taken along the line 12—12 of FIG. 11; and FIG. 13 is a plan view of a locating disk for positioning the medial support straps.

Corresponding reference characters indicate corresponding components throughout the several views of the drawings.

DETAILED DESCRIPTION OF THE PREFERRED EMBODIMENT

The knee brace of the present invention is generally shown in the medial and lateral views of FIGS. 1 and 2, respectively. However, before describing the knee brace in detail, it will be helpful to consider a knee joint and the types of forces to which a knee is subjected, that are addressed by the present invention.

Referring now to FIGS. 7 and 8, a front or anterior view of a knee joint illustrates an upper knee component 2 extending from the lower portion of the femur, and a lower knee component 4 at the upper portion of the tibia. A medially-directed force F, applied to the lateral side of the knee joint, causes medial portions of the knee components 2, 4 to separate, as indicated in FIG. 8. The angle of separation, a, serves as a convenient indicator for the performance of knee brace 10. Tests on cadavers have indicated that tearing of ligaments and cartilage about the medial portion of a knee joint begin to occur with an angle of separation lying between 10° and 20°. In general, an angular separation of 15° has been determined as the average value on cadavers at which knee ligaments and cartilage begin to tear. Tests on cadavers appear to show that the medial collateral ligament begins to tear when the knee joint opens 1.5 to 2.0 cm and that the anterior cruciate ligament begins to tear thereafter. Manifestly, the amount of opening before tearing depends on the amount of stretch the particular ligament can endure before failing and the amount of stretch will vary substantially from individual to individual and generally decreases as an adult becomes older. The medial collateral ligament appears to be more susceptible to tearing than outer or lateral ligaments because blows to the knee are more often delivered to the outside rather than to the inside of the knee thereby causing the medial side of the knee to open. With a unilateral knee brace applied to the lateral side of knee as shown in FIG. 7, the pivot axis or point about which the knee opens is shifted outwardly from the leg bones, as shown in FIG. 8, to the pivot axis of the brace, as shown in FIG. 7.

The brace of the present invention offers a wearer between 20 and 30 times greater resistance to knee separations of 10° or more over conventional unilateral braces. According to impact testing, the brace of the present invention provides a 200% to 300% increase in knee stiffness compared to a 10% to 20% increase in knee stiffness provided by conventional unilateral knee braces, allowing the wearer of the knee brace to successfully withstand two to three times the medially-directed force before experiencing medial collateral ligament rupture. The reported two to threefold increase in knee stiffness (the ability to resist opening under force) is a surprising improvement in unilateral knee brace performance, and represents a significant advance in the art, especially since the bulk and weight of the knee brace is not increased. More importantly, the brace becomes stiffer than the knee at the point of ligament tear.

Referring now to FIGS. 1 and 2, the knee brace of the present invention is indicated generally at 10. FIG. 1 shows a pliable support assembly 12 comprising medial straps 14 which are positioned adjacent the medial or inside portion of the wearer's leg. FIG. 5 shows assembly 12 in greater detail. FIG. 2 shows a hinged support 16 which is preferably positioned adjacent the lateral or outside portion of the wearer's leg (hinged support 16 could also be located on the medial side of the leg to also protect against medial opening). Both hinged and flexible support assemblies extend above and below the knee joint, and are secured to the wearer's leg by upper and lower brace assemblies or cuff members indicated generally at 18, 20, respectively.

Referring to FIGS. 2 and 7, the hinged support 16 includes an upper rigid hinged plate member indicated generally at 22, which is concave at its upper leg-engaging portion 24, and which has a lower flat semicircular plate 26. A laterally-offset transition 28 joins upper and lower portions 24, 26. A lower rigid hinged plate member, indicated generally at 30, is similarly configured to have a lower concave leg-engaging portion 32, a flat semicircular plate 34, and a laterally-offset transition 36. The two plates are secured together by a rivet or pivot pin 38 and a pair of washers 39 in a manner to permit pivotal movement and restrain any lateral movement. Offset transverse portions 28, 36 hold the pivotal joint away from the wearer's knee to avoid any unwanted contact therewith.

Further details of the construction and operation of the hinged support described above may be found in the aforementioned U.S. Pat. No. 3,528,412 issued to Robert F. McDavid, which patent is herein incorporated by reference to the extent necessary for an understanding of the present invention.

The term "rigid" as used herein to refer to hinge plates 20, 22, denotes the axial incompressibility of those members, despite the fact that the hinge plates may be slightly flexible in directions normal to their axes. For example, in the preferred embodiment, hinge plates 20, 22 are made of polycarbonate plastic material which offers some conformance to the outer contour of a wearer's leg. The hinge plates may, however, be formed of metal or other material so as to be inflexible in any direction.

In the preferred embodiment, a simple pinned connection is used to hinge the plates 20, 22 together. Other forms of hinged connection are also contemplated by the present invention. For example, the hinge plates may be geared together to offer a so-called polycentric movement, as is known in the art. Other hinged connections allowing rotation or bending in multiple directions are also possible.

It is desirable to cover both the inside and outside surfaces of the hinged support with a resilient material, such as sponge rubber, since the upper and lower hinge plates 22, 30, are formed of hard, rigid plastic material which applies a compressive loading to the wearer's leg. It will be appreciated that the hard, rigid quality of the hinge plate material is necessary if compressive forces applied to the outside of the leg as well as tension forces resulting at the inside of the knee joint are to be successfully withstood. Although the foam material is not shown in the drawings, those skilled in the art will readily understand how such foam is to be applied about the hinge plates 22, 30. For example, the hinge plates can be inserted within sleeves of foam material. This technique is particularly advantageous when used to cover the semicircular plates 26, 34 located immediately adjacent the knee joint. It is also desirable to cover the inside portion of the pivot pin 38 with a foam washer 40 to provide added protection.

Referring now to FIGS. 3 and 4, hinged support 16 extends between cuff members 18, 20 which secure the hinged support to the wearer's leg. The upper cuff 18 comprises a leg band 42 preferably formed e t foam overlaid with an outer covering of "VELCRO" material which provides releasable engagement with a "VELCRO" tab 44 located at one end of the band. The cuff 18 further comprises a rigid, i.e, non-elastic, stretch-resistant pocket 46 for receiving the upper leg-engaging portion 24 of hinge plate 22. Pocket 46 is preferably formed of a non-stretch fabric material, and is sewn directly to leg band 42 by stitching 47. "velcro" material, not shown in the Figures, is provided on an outside surface of leg-engaging portion 24 and an inside surface of pocket 46 to maintain engagement therebetween. In addition, pocket 46 is dimensioned for close-fitting retention of leg-engaging portion 24.

Lower cuff 20 is similarly constructed, having a similar band 52, "VELCRO" tab 54, and a pocket 56 which also provides close-fitting reception of the lower leg engaging portion 32. Pocket 56 is sewn directly to band 52 by stitching 57.

In accordance with the present invention, a unilateral knee brace is provided with enhanced resistance to opening of the knee on the medial side when blows are delivered to the lateral side of the knee to either prevent tearing of the medial collateral ligament or to reduce the amount of tearing of this ligament and of the anterior cruciate ligament that would otherwise be experienced without the use of this invention. This is achieved by the use of anchored tension means or members 14 which resist forces tending to open the medial side of the knee to an extent that will damage the ligaments. More specifically, the tension members or straps 14 are abutted against the medial side of the knee which has less flesh than the outer side of the knee and, as the knee bones tend to open, they push against the strap members at the juncture, and apply generally equal tension or equal forces to the strap members which will resist further opening of the knee joint. Herein, the straps are substantially non-extensible cords or straps which do not elongate substantially under the loads involved. The straps will pull on their anchored ends which are firmly attached to the rigid upper and lower plate members 22 and 26. The now tensioned straps 14 are thus holding the medial side of the knee against opening to the extent that it would if no straps were present, or if the straps were elastic and stretched easily under the loads applied thereto. In a sense, the tensioned straps 14 may be thought of as acting as additional ligament or ligament enhancers which resist opening of the knee at the medial side. Also, it will be seen that the tensioned straps connect the medial side of the knee to the lateral side of the knee at which the support plates are located to resist opening of the medial side of the knee. From the foregoing, it can be seen why a knee braced with the present invention is said to be two or three times stiffer with respect to medial opening.

Upper cuff 18 further comprises latching straps 60, 62 which are sewn at 63 at one end onto pocket 46 (see FIGS. 4, 11 and 12) and which have buckles 64 at their other, free ends (see FIG. 3). Improved stiffness of the knee brace of the present invention results directly from the efficient transmission of tension forces in straps 14 to leg-engaging portions 24, 32. The connection of straps 14 to the leg-engaging portions of the hinged support is such that a minimum of knee opening movement is experienced before the pliable support assembly 12 is tensioned at the time of impact. If only 1.5 to 2.0 cm of knee opening causes damage then it is desirable to have the straps tensioned as soon as possible. Accordingly, the present invention provides latching straps 60, 62 which are formed of a non-elastic, i.e., stretch-resistant, material. Also, pocket 46 must be close-fitting for slip-free and dislocation-free retention of leg engaging portion 24, and latching straps 60, 62 must be rigidly secured to cuff 18 immediately adjacent leg engaging portion 24, in a dislocation-free manner.

In the illustrated embodiment, as described above, latching straps 60, 62 are sewn directly onto pocket 46. Sewing is preferred because of its rigid, "no-play" securement, and other fastening arrangements ar contemplated by the present invention. In each arrangement, however, care is be taken to likewise prevent any "play" or dislocation of the strap under load.

In the preferred embodiment, shown in FIGS. 11 and 12, straps 60, 62 are formed of one length of strap material. Both ends of the material are sewn on the inside of pocket 46, with one end of the material being sewn on the outer part of the pocket, and the other end sewn on the inner part of the pocket (that part closest the wearer's leg). In crossing from outer to inner parts, the material crosses over one end of hinge plate 22, so as to efficiently apply a compressive load along the axis of the hinged support member as well as applying a force component to hinge plate 22.

Referring Now to FIG. 9, straps 60, 62 are looped at one end through slots 100 in hinge plate 22 and are looped at their other end through buckle 64. The straps are sewn together at their center portion at 104. Alternatively, a medial strap 14 can be threaded through slot 100 and secured at its free ends to a buckle 64. In either alternative the strap is conveniently looped around an edge portion of plate 22 for captive retention thereon. The buckled alternative offers the further advantage of being removable, allowing withdrawal of hinge plate 22 from a pocket similar to that shown in FIG. 2 but having slits formed therein to allow threading of the straps therethrough. Referring to FIG. 10, in yet another alternative, loops 106 of leather or the like can be threaded around a buckle, and their free ends riveted or screwed directly to hinge plate 22, as indicated at 108.

Referring now to FIG. 3, medial straps 14 are sewn at one end to pocket 56 of lower cuff 20 via stitching 63. The other, free ends of medial straps 14 are finished in a conventional manner for latching with buckles 64. It is important that medial straps 14 be formed of non-elastic, stretch-resistant material, and that they be rigidly affixed to pocket 56 immediately adjacent leg-engaging portion 32, in a slip-free, dislocation-free manner. According to the present invention, latching straps and buckles, similar to straps 60, 62 and buckles 64 can also be provided adjacent pocket 56. Any buckles so employed in the latching straps, as well as buckles 64, must be capable of providing rigid securement to the medial straps so as to eliminate any play, slipping, stretching or other dislocation in the overall pliable support assembly 12, when that assembly is placed under a tension load. The rigid, or dislocation-free features described above ensure that any forces applied to medial straps 14 are directly coupled to hinge plates 22, 30 without any intervening stretch, play, or the like dislocation that would absorb all or some of the applied tension force. As will now be appreciated, any stretch or play in pliable support assembly 12 during impact will allow medial portions of the knee joint to open in the manner indicated in FIG. 8. The precautions in construction of the knee brace of the present invention, to provide a lossless transmission of tension forces to the leg-engaging portions, are essential to prevent such opening, and directly result in the significantly improved performance described earlier.

Referring now to FIG. 5, medial straps 14 are shown in greater detail wherein the two straps 14 are crossed in an X-like configuration. Each end of the "X" is adjustable, offering an orthopedic specialist the ability to provide rotational control for certain ligaments by tensioning the straps different, carefully set amounts. Straps 14 may be sewn together at the center of the "X", as illustrated in FIG. 5, but in the preferred embodiment, they are threaded through slots 120 of a locating disk 122 (see FIG. 13). The disk is preferred over sewing since straps 14 can be sewn at one end to cuff 20 (as shown in FIG. 3) and can still accommodate a range of leg sizes while assuring that the "X" is centered on the knee joint. Disk 122 has an outer vinyl layer 126, a conformable plastic core 128, and a soft foam inner layer 130. Plastic core 128 is flexible only to the extent necessary to conform to the external contour of the wearer's knee. Slots 132 form a bar 134. A strap 14 overlays the vinyl layer 130 and is threaded under bar 134. Disk 122 can be slid along each strap 14 so as to always be located at the center of the "X".

The locating disk 122 is preferred in that it assists in holding the straps against sliding away from a spot exactly opposite the pivot pin. Also, the locating disk 122 assists the wearer in correctly fitting the brace onto his leg. That is, the wearer will extend his leg to the maximum and locate the disk 122 immediately opposite the knee joint and pivot pin axis, and will then tighten the straps 14 securely to make sure there is no play in the straps. With the locating disk 122 at this position, each of the straps is located to take an equal tension load and to assist equally in resisting an opening of the knee.

FIG. 6 shows an alternative embodiment of the pliable support assembly, which is generally indicated at 12', wherein two V-shaped straps 70, 72 are arranged with opposed apices 74, 76 joined together through an intermediate strap 77. As with support assembly 12, all materials making up the alternative support of FIG. 6 must be non-elastic or stretch resistant, and when formed of multiple pieces, must be secured together without slip or play. In the embodiment of FIG. 6, strap 78, comprised of conventional fabric webbing, is sewn to the apices 74, 76 of straps 70, 72, the straps being folded to form the V-shaped configuration. The numeral 78 is applied to the center of strap 77 which generally opposes pivot pin 38 in the completed assembly, so that the apices 74, 76 are held in place against a medial portion of the wearer's leg, on either side of the knee joint. As in the X-shaped embodiment of FIG. 5, the relative orientation of hinge support 16 to pliable support 12 and to the wearer's knee joint is maintained by cuff members 18, 20 throughout a range of motion of the wearer's knee. Pliable support assembly 12' is shown comprised of three pieces in the illustrated embodiment. Other ways of sewing or otherwise forming the straps (as by glue or other welding) to achieve the same general configuration is also contemplated by the present invention.

In either embodiment of FIGS. 5 or 6, the straps of the pliable support assembly must include a portion immediately adjacent the wearer's knee joint, directly opposite pivot pin 38, since that is the point of application of medially-directed force F to the pliable support assembly. Other strap configurations, other than the "X" or the separated-V construction of FIG. 6, and are contemplated by the present invention. For example, a crisscross latticework made up of a vertical array of X-shaped configurations may be employed. Or arcuate straps, joined together to generally resemble an X-shape, may be employed. However, no matter which strap design is chosen, the most efficient transfer of forces in the straps to the leg-engaging portions of plates 24, 32 requires that strap portions be located generally opposite pivot pin 38.

Retaining straps 82, 84 having an outer "velcro" covering and "velcro" tabs 86, 88 at their ends, are provided for cuffs 18, 20. Pockets 46, 56 are each provided with formed straps 90, 92 to which the retaining straps 82, 84 are inserted for securement therein. Strap 82 for example, is wrapped about the outside surface of cuff 18 after pliable support assembly 12 has been attached thereto. Strap 82 and especially strap 84 serve to hold the knee brace in their proper position, on the wearer's leg, to keep the brace from migrating down the leg. Strap 84 functions in a similar manner, retaining the lower ends of medial straps 14 in place upon wrapping about lower cuff 20.

When force F is applied to the outside of the knee joint, medial portions of the knee joint would tend to separate in the manner shown in FIG. 8, but for the brace of the present invention, which maintains medial portions of the knee joint together, absorbing the tensioning forces experienced there during impact. That is, straps 14 of the knee brace are placed in tension as force F is absorbed by the brace. Force F also applies a direct compression to the upper and lower portion of the wearer's leg, which is transmitted by leg-engaging portions 24, 32 located remote from the knee joint. The tension forces applied to straps 14 are resisted because the ends of the straps are anchored to the rigid leg-engaging portions of the brace. These non-extensible, anchored tension straps provide a lightweight, inexpensive medial support. Thus, according to the present invention, the two to threefold increase in knee stiffness and the twenty to thirty times improved resistance to knee joint opening over existing unilateral knee braces is attributed to having a snug fit of the knee brace to the wearer's leg, and the tension members which hold the inner portion of knee against opening sufficiently to tear a ligament. It is clear from the teachings of the present invention that substantial slippage or stretching of straps 14 would defeat the surprising performance results attained by the brace of the present invention.

In some instances, the unilateral knee brace is secured to the leg with wraps of adhesive tape before each usage. It has been found that when one tightly tapes the upper and lower plates 22 and 26 to the leg, the unilateral knee brace is actually stiffer and the tension members or straps 14 are more quickly effective than when the elastic cuff members are used.

The brace of the present invention has been described in connection with its principal usage as a knee brace for prophylactic protection in sports. However, this unilateral knee brace may be used also for functional protection and for rehabilitation protection and this use still falls within the purview of the appended claims. In some instances, it may be desired to preload one side or some straps to provide rotational support for a knee undergoing rehabilitation.

It may therefore be seen that the present invention provides a lightweight knee brace that utilizes a slip-free, stretch-free flexible support on the medial portion of a wearer's leg so as to provide an enhanced stiffness against medially-directed forces which tend to separate the medial portion of a wearer's knee. The knee brace of the present invention accordingly offers improved performance in preventing a knee joint from opening at its medial portion, thereby constraining a wearer's knee to its natural position and motion.

Those skilled in the art will readily appreciate that the medial strap 14 operates as an auxiliary medial collateral ligament, offering augmentation of that ligament, since the anterior portions of the straps tighten as the knee is flexed in a normal motion. As indicated in the above, tension forces in straps 14 are transferred diagonally across the knee joint for controlled dissipation in a hinged support plate.

While the invention has been described in connection with a preferred embodiment, it will be understood that it is not intended to limit the invention to that embodiment. On the contrary, it is intended to cover all alternatives, modifications and equivalents included within the scope of the appended claims.

What is claimed is:

1. An improved knee brace for constraining a wearer's knee to its natural position and motion despite tension forces tending to open medial portions of the knee joint upon application of an applied compressive force to lateral portions of the knee, comprising:
    a hinged support means including a lower plate member extending below the wearer's knee and an upper plate member extending above the wearer's knee and upper plate member attaching above the wearer's knee, and means for pivotally attaching said lower and upper plate members adjacent the wearer's knee;
    support means, including straps of pliable stretch-resistant material attached to the upper and lower plate members and lying along lines which intersect the medial center of the knee, laterally opposite said hinged support means;
    means for connecting the straps together so as to support the medial center of the wearer's knee and so as to maintain the point of intersection generally at the medial center of the knee throughout normal range of motion of the knee; and
    lower and upper securement means for securing said hinged support means to a lateral portion of the wearer's leg, and for stretch-resistant securing of said straps to respective plate members, whereby forces tending to open the medial portion of the wearer's knee are transmitted in tension through said straps to said plate members at points remote from the wearer's knee joint.

2. The knee brace of claim 1 wherein said portions of said pliable support means comprise lower and upper generally V-shaped portions extending below and above the wearer's knee, respectively, the V-shaped portions having generally opposed, joined apices with each V-shaped portion having said spaced first and second free ends.

3. The knee brace of claim 2 wherein each securement means includes a stretch-resistant assembly having a place-retaining means for retaining gone of said plate members and immediately adjacent attaching means for attachment to the free ends of one of said v-shaped portions.

4. The knee brace of claim 2 wherein said securement means includes means for attaching said free ends of one of said V-shaped portions directly to one of said plate members.

5. The knee brace of claim 2 wherein each said securement means comprises a cuff-like assembly of pliable material for securement around a wearer's leg.

6. The knee brace of claim 5 wherein the apices of the V-shaped portions are connected together to form a generally X-shaped support member.

7. The knee brace of claim 5 wherein the apices of the V-shaped portions are connected together through an intermediate strap-like member which overlies the medial center of the knee so as to laterally oppose said hinged support means.

8. The knee brace of claim 1 wherein said pliable support means are joined to locating means overlying a medial portion of the wearer's knee to form a generally X-shaped support member having a point of crossing located on the medial center of the knee joint.

9. The knee brace of claim 1 wherein said upper and lower plate members of said hinged support include concave leg-engaging free ends that contact substantially only the lateral portions of the wearer's leg.

10. The knee brace of claim 1 wherein each securement means includes a stretch-resistant body having a plate-retaining means for retaining one end of said plate member and said body having means for joinder with said support means.

11. In a unilateral knee brace, the combination comprising:
    an upper support means for attachment to the wearer's leg above the knee joint at the lateral side of the leg;
    a lower support means for attachment to the wearer's leg below the knee joint at the lateral side of the leg;
    hinge means hinging the upper and lower support means for pivoting movement with bending of the knee;
    tension members of bendable stretch-resistant material connected to the upper and lower support means and lying along lines which intersect the medial center of the knee joint; and
    means for connecting the tension members together so as to support the medial center of the knee joint against opening to the extent that ligaments are torn when a blow is applied to the lateral side of the knee and so as to maintain the point of intersection generally at the medial center of the knee joint throughout a normal range of motion of the knee.

12. A knee brace in accordance with claim 11 in which said tension members are non-elastic straps having the general shape of an X with the center of the X located at the medial center of the knee joint.

* * * * *

UNITED STATES PATENT AND TRADEMARK OFFICE
CERTIFICATE OF CORRECTION

PATENT NO. :  4,805,606

DATED : February 21, 1989

INVENTOR(S) : Robert F. McDavid, III

It is certified that error appears in the above-identified patent and that said Letters Patent is hereby corrected as shown below:

On the title page after "Assignee:" change "Terrence" to --Terence--.

On column 5, line 4, after "formed" insert --of resilient--.

On column 5, line 5, before "foam" delete "e t".

On column 5, line 8, change "i.e." to --i.e.,--.

On column 5, line 13, change ""velcro"" to --"VELCRO"--.

On column 6, line 14, change "ar" to --are--.

On column 6, line 16, after "is" insert --to--.

On column 6, line 29, change "Now" to --now--.

On column 8, line 13, change ""velcro"" to --"VELCRO"--.

On column 8, line 14, change ""velcro"" to --"VELCRO"--.

On column 9, line 34 and 35, delete "and upper plate member attaching above the wearer's knee".

UNITED STATES PATENT AND TRADEMARK OFFICE
CERTIFICATE OF CORRECTION

PATENT NO. : 4,805,606
DATED : February 21, 1989
INVENTOR(S) : Robert F. McDavid, III It is certified that error appears in the above-identified patent and that said Letters Patent is hereby corrected as shown below:

On column 9, line 46, after "throughout" insert --the--.

On column 10, line 3, change "place" to --plate--.

On column 10, line 3, change "gone" to --one--.

On column 10, line 5, change "v-shaped" to --V-shaped--.

Signed and Sealed this

Twenty-eighth Day of November 1989

*Attest:*

JEFFREY M. SAMUELS

*Attesting Officer*   *Acting Commissioner of Patents and Trademarks*